(12) United States Patent
Rozgic et al.

(10) Patent No.: US 10,355,192 B2
(45) Date of Patent: Jul. 16, 2019

(54) AUTONOMOUS THERMOELECTRIC ENERGY HARVESTING PLATFORM FOR BIOMEDICAL SENSORS

(71) Applicant: The Regents of the University of California, Oakland, CA (US)

(72) Inventors: Dejan Rozgic, Los Angeles, CA (US); Dejan Markovic, Palo Alto, CA (US)

(73) Assignee: The Regents of the University of California, Oakland, CA (US)

( * ) Notice: Subject to any disclaimer, the term of this patent is extended or adjusted under 35 U.S.C. 154(b) by 242 days.

(21) Appl. No.: 15/525,278

(22) PCT Filed: Nov. 6, 2015

(86) PCT No.: PCT/US2015/059605
§ 371 (c)(1),
(2) Date: May 8, 2017

(87) PCT Pub. No.: WO2016/073944
PCT Pub. Date: May 12, 2016

(65) Prior Publication Data
US 2017/0338394 A1 Nov. 23, 2017

Related U.S. Application Data

(60) Provisional application No. 62/076,431, filed on Nov. 6, 2014.

(51) Int. Cl.
*H02M 3/335* (2006.01)
*H02M 1/36* (2007.01)
(Continued)

(52) U.S. Cl.
CPC .............. *H01L 35/32* (2013.01); *A61N 1/372* (2013.01); *G01K 7/02* (2013.01); *H01L 35/28* (2013.01);
(Continued)

(58) Field of Classification Search
CPC ..... H02M 3/33507; H02M 1/36; H01L 35/32; H01L 35/28; A61N 1/372; G01K 7/02
(Continued)

(56) References Cited

U.S. PATENT DOCUMENTS 6,131,581 A 10/2000 Leysieffer et al.
2010/0270996 A1 10/2010 Ramadas et al.
(Continued)

FOREIGN PATENT DOCUMENTS

WO 2016073944 A1 5/2016

OTHER PUBLICATIONS

Machado et al., Fully integrated inductive ring oscillators operating at VDD below 2kT/q, Analog Integrated Circuit Signal Processing, vol./Issue 82, pp. 5-15 (Year: 2014).*
(Continued)

*Primary Examiner* — Jayne L Mershon
(74) *Attorney, Agent, or Firm* — KPPB LLP

(57) ABSTRACT

Thermoelectric energy harvesting systems in accordance with embodiments of the invention enable energy harvesting. One embodiment includes a thermoelectric energy harvesting (TEH) system comprising a TEH comprising a thin-film array-based TEH source; start-up mode circuitry comprising: an upper branch comprising: a mode switch configured to allow selection of the upper branch; an inductive-load ring oscillator (ILRO); a charge pump configured to receive an input from the ILRO and output current, where output current is utilized to charge an upper branch capacitor; a lower branch comprising: an inductor; an active diode configured to transfer energy stored in the inductor to an output capacitor; maximum-power-point tracking (MPPT) mode circuitry, where the MPPT loop comprises: a mode control unit; a gate controller; a clock generator configured to generate at least one control signal; an analog-domain (Continued)

MPPT unit configured to receive the at least one generated control signal.

14 Claims, 18 Drawing Sheets

(51) Int. Cl.
    *H01L 35/32*     (2006.01)
    *H01L 35/28*     (2006.01)
    *A61N 1/372*     (2006.01)
    *G01K 7/02*     (2006.01)
    *H01L 35/30*     (2006.01)

(52) U.S. Cl.
    CPC ............ *H02M 1/36* (2013.01); *H02M 3/335* (2013.01); *H01L 35/30* (2013.01)

(58) Field of Classification Search
    USPC ...................................................... 363/21.12
    See application file for complete search history.

(56) References Cited

U.S. PATENT DOCUMENTS

| | | |
|---|---|---|
| 2011/0254514 A1 | 10/2011 | Fleming |
| 2012/0192908 A1 | 8/2012 | Kline |
| 2013/0328416 A1 | 12/2013 | Whitworth et al. |
| 2014/0233270 A1* | 8/2014 | Desai ................ H02M 3/33523 363/21.12 |

OTHER PUBLICATIONS

International Preliminary Report on Patentability for International Application No. PCT/US2015/059605, Search completed May 9, 2017, dated May 18, 2017, 5 pages.

International Search Report and Written Opinion for International Application No. PCT/US2015/059605, Search completed Feb. 19, 2016, dated Feb. 19, 2016, 7 pages.

"Laird Technology", Laird Technology, Dec. 29, 2013, retrieved from https://web.archive.org/web/20131229091550/http://www.lairdtech.com:80/default.aspx#.WYjb-ojyuUk on Aug. 8, 2017, 2 pages.

Carlson et al., "A 20 mV Input Boost Converter With Efficient Digital Control for Thermoelectric Energy Harvesting", IEEE Journal of Solid-State Circuits, vol. 45, Issue 4, Apr. 2010, pp. 741-750.

Chen et al., "A 95mV-startup step-up converter with Vth-tuned oscillator by fixed-charge programming and capacitor pass-on scheme", 2011 IEEE International Solid-State Circuits Conference, Feb. 20-24, 2011, San Francisco, CA, USA, pp. 216-218.

Im et al., "A 40mV transformer-reuse self-startup boost converter with MPPT control for thermoelectric energy harvesting", 2012 IEEE International Solid-State Circuits Conference, Feb. 19-23, 2012, San Francisco, CA, USA, pp. 104-106.

Machado et al., "On the Minimum Supply Voltage for MOSFET Oscillators", IEEE Transactions on Circuits and Systems I: Regular Papers, vol. 61, Issue 2, Feb. 2014, pp. 347-357.

Ramadass et al., "A Batteryless Thermoelectric Energy-Harvesting Interface Circuit with 35mV Startup Voltage", 2010 IEEE International Solid-State Circuits Conference—(ISSCC), Feb. 7-11, 2010, San Francisco, CA, USA, pp. 486-487.

Tang et al., "A fully electrical startup batteryless boost converter with 50mV input voltage for thermoelectric energy harvesting", 2012 Symposium on VLSI Circuits (VLSIC), Jun. 13-15, 2012, Honolulu, HI, USA, pp. 196-197.

* cited by examiner

| Reference | [1]+ | [2] | [3]++ | [4] | A system in accordance with an embodiment of the invention |
|---|---|---|---|---|---|
| Process | 0.13μm | 0.35μm | 0.13μm | 65nm | 65nm |
| Startup mechanism | External voltage | Mechanical | White noise | Electrical | Electrical |
| Min $V_{start-up}$ | 650mV | 35mV | 40mV | 50mV | 65mV |
| Regulated $V_{out}$ | 1V | 1.8V | 2V | 1.2V | 1.8V |
| Peak efficiency end-end (conv.) | 63% e-e (75% cnv) | 58% e-e (91% cnv) | 61% e-e (N/A cnv) | N/A (73% cnv) | 88% e-e (92% cnv) |
| Off-chip L+C | 1+3 | 3+4 | 2+5 | 3+4 | 1+2 |

$V_{start-up}$ refers to $V_{TEH}$
(e-e) end-to-end
(cnv) converter (+) no MPPT
(++) uses transformer

[1] 22 — 58x →
[2] 34 — 37x →
[4] 162 — 7.9x →
This Work 1285
780μW/cm² in-vivo (3.5K)

Regulated Power Density @ΔT=4K (μW/cm²)

*FIG. 8*

| [1] | [2] | [3] | [4] | [1] |
|---|---|---|---|---|
| Battery used for start-up → not autonomous | Mechanical start-up → initial vibrations → limited apps | Transformer used → heavy system | Low efficiency of the start-up block | Post-fabrication $V_{TH}$ trimming required |
| No MPPT | Efficiency declining above $V_{TEG}$=80mV | Very low efficiency below 100mV input | MPPT from [2] used | Storage 10nF (stability issue) |
| Storage 10nF (stability issue) | Bulky (10cm²) → large volume → biomedical implants not possible | $\phi_{1\text{-}2}$ (f=50Hz) applied externally → slow MPPT (sec-range) → needs pure DC source | 3-step architecture | No MPPT |
| Min $\Delta T$=4K for circuit operation | | Peak efficiency @$V_{TEG}$=300mV → need $\Delta T$=6-7K | 3 inductors → bulky (6.3cm²) → biomedical implants not possible | Regulation time ~300ms |
| | | | | Tested with ideal voltage source ($R_{TEG}$) → can't measure e-e efficiency |

FIG. 12

AUTONOMOUS THERMOELECTRIC ENERGY HARVESTING PLATFORM FOR BIOMEDICAL SENSORS

CROSS REFERENCE TO RELATED APPLICATIONS

This application is a national stage of PCT Patent Application No. PCT/US2015/059605, entitled "Autonomous Thermoelectric Energy Harvesting Platform For Biomedical Sensors" to Rozgic et al., filed Nov. 6, 2015, which claims priority to U.S. Provisional Patent Application No. 62/076,431, entitled "Autonomous Thermoelectric Energy Harvesting Platform for Biomedical Sensors" to Rozgic et al., filed Nov. 6, 2014, the disclosures of which are incorporated herein by reference in their entirety.

FIELD OF THE INVENTION

The present invention generally relates to energy harvesting and more specifically to autonomous thermoelectric energy harvesting platforms for biomedical sensors.

BACKGROUND

A so-called thermoelectric effect describes energy conversion from a thermal gradient to electrical energy, where a temperature difference (i.e. thermal gradient) between one or more conducting materials results in heat flow and the diffusion of charge carriers. Typically, the flow of charge carriers between two regions of differing temperatures can create a voltage difference that allows for energy harvesting.

Prior systems have focused on improving converter efficiency and migrating from mechanical to electrical start-up circuits. However, harvesting energy in natural environments such as in biomedical applications can be challenging due to limited (<2K) thermal gradients. Further, in biomedical implants and wearable electronics, it is typically difficult to achieve sufficient gradient from the harvesting interface and also include a highly-efficient power management system.

SUMMARY OF THE INVENTION

Thermoelectric energy harvesting systems in accordance with embodiments of the invention enable energy harvesting. One embodiment includes a thermoelectric energy harvesting system comprising a thermoelectric energy harvester (TEH) comprising a thin-film array-based TEH source and a heat sink; start-up mode circuitry connected to the TEH comprising: an upper branch comprising: a mode switch configured to allow selection of the upper branch; an inductive-load ring oscillator (ILRO) comprising a cross-coupled pair, where the ILRO is configured to operate in weak inversion conditions; a charge pump configured to receive an input from the ILRO and output a current, where the output current is utilized to charge an upper branch capacitor; a lower branch comprising: an inductor; an active diode configured to transfer energy stored in the inductor to an output capacitor; maximum-power-point tracking (MPPT) mode circuitry comprising an MPPT controller configured to activate an MPPT loop, where the MPPT loop comprises: a mode control unit; a gate controller; a clock generator configured to generate at least one control signal; an analog-domain MPPT unit configured to receive the at least one generated control signal.

In a further embodiment, the mode switch includes a native-NMOS that is initially set as ON.

In another embodiment, the cross-coupled pair utilizes analog transistors.

In further embodiment again, the charge pump is an eight stage dynamic change-transfer-switch charge pump.

In still another embodiment, the mode control unit comprises a negative voltage generator, mode sensing circuitry, and reference circuitry.

In a yet further embodiment, the negative voltage generator is configured to shut down the mode switch and the start-up circuitry.

In yet another embodiment, the analog-domain MPPT unit comprises a voltage sensor, output regulator, a pulse width modulation driver, and an inversion matrix unit.

In further embodiment again, the inductor is off-chip.

In another embodiment again, the output capacitor is off-chip.

In further additional embodiment, the start-up mode stays active until the output capacitor has a value of 0.8V.

In a still yet further embodiment, the thermoelectric energy harvesting system further comprising a load powered by the output capacitor.

In still yet another embodiment, the load is a neural recording system.

In another additional embodiment, the upper branch periodically turns ON to boost the energy stored in the output capacitor.

In still yet further embodiment again, the MPPT mode stay active until $C_{out}$ is charged to a predetermined value based upon the at least one generated control signal.

BRIEF DESCRIPTION OF THE DRAWINGS

FIG. 8 is a chart that illustrates comparisons between a thermoelectric energy harvesting system with various prior works in accordance with an embodiment of the invention.

FIG. 12 is a chart illustrating drawbacks of previous works in accordance with an embodiment of the invention.

DETAILED DESCRIPTION OF THE DRAWINGS

Turning now to the drawings, an autonomous thermoelectric energy harvesting platform for biomedical sensors in accordance with embodiments of the invention are illustrated. In many embodiments, the thermoelectric energy harvesting system includes a thermoelectric energy harvester (TEH) having a thin-film array-based TEH source and an associated heat sink. Typically, current generated by the TEH flows from the TEH to a start-up branch comprising various circuit components as further described below. In several embodiments, the TEH can be connected to a start-up branch having an upper branch and a lower branch, where the system utilizes a particular branch as further described below. In various embodiments, the system can also include a maximum-power-point tracking (MPPT) mode that can include an MPPT controller and an MPPT loop having a mode control unit, a gate controller, a clock generator and an analog-domain MPPT unit as further discussed below. In many embodiments, the MPPT circuitry allows for charging an output capacitor to a desired value to power various biosensor functionalities including (but not limited to) powering a neural recording interface.

Autonomous thermoelectric energy harvesting systems in accordance with embodiments of the invention can be optimized for energy and conversion efficiencies. In a variety of embodiments, a TEH source integrated with a heat-sink can be implemented in a variety of spaces including (but not limited to) a space of 0.83 cm$^2$. Further, the MPPT mode can be realized in an analog domain for high efficiency and fast (<20 ms) tracking time. In various embodiments, power can be managed utilizing one off-chip inductor. In many embodiments, systems in accordance with embodiments of the invention can have 68% end-to-end peak efficiency (92% converter efficiency), at 4K. As illustrated further below, a 645 µW regulated output power can be harvested from the head of a rat (effective 3.5K) implanted with TEH, demonstrating true energy autonomy in a real environment.

Although discussed in the context of biomedical sensors, the proposed systems and methods can be utilized with a variety of implementations for thermoelectric energy harvesting such as (but not limited to) wearable electronics and thus are not limited to biomedical sensors. Autonomous thermoelectric energy-harvesting systems in accordance with embodiments of the invention are further discussed below.

Theroelectric Energy Harvesting System Architectures

Figure 1:
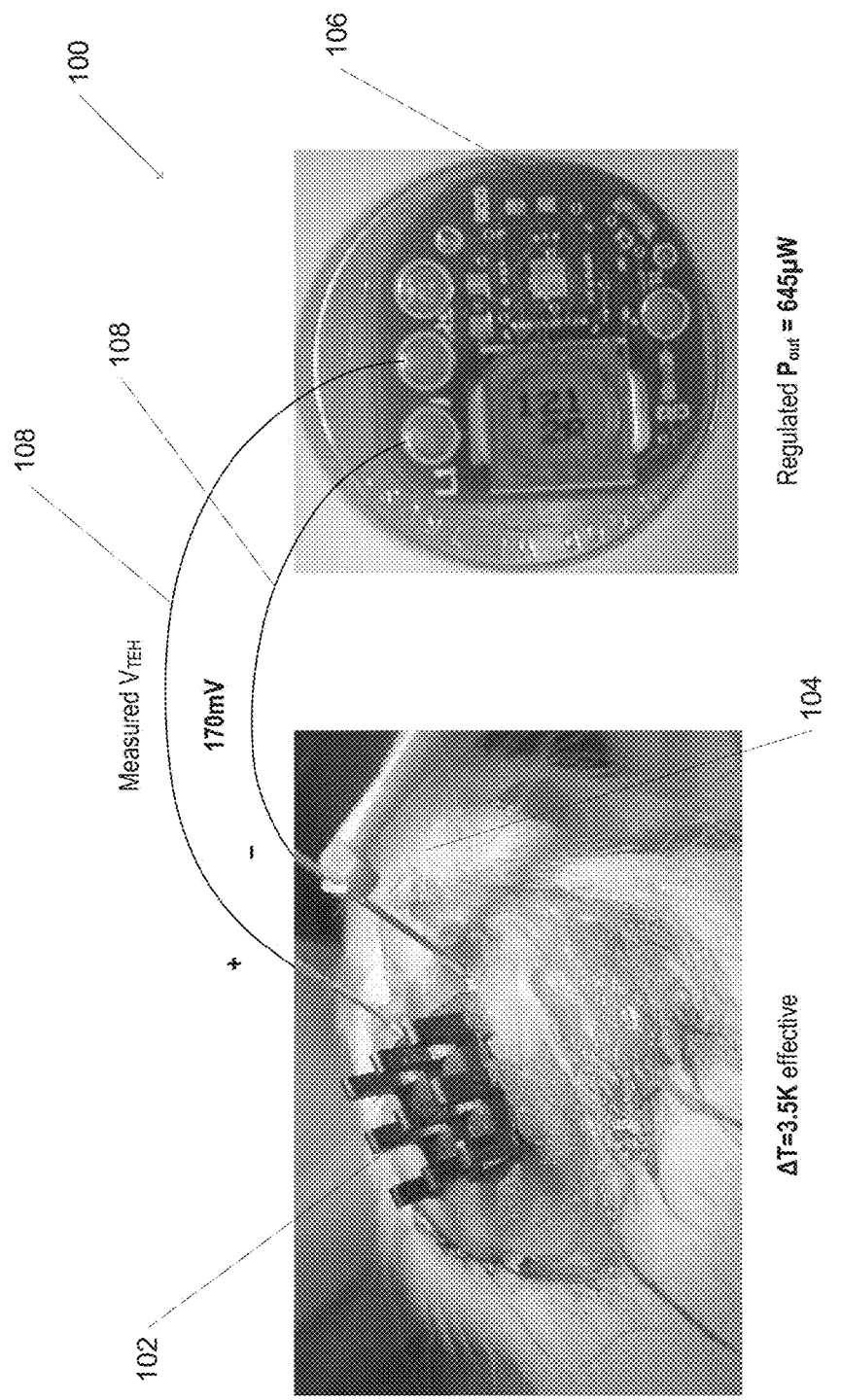
FIG. 1 illustrates a thermoelectric energy harvesting system implanted on a test subject in accordance with an embodiment of the invention.

A TEH system implanted in a test subject in accordance with an embodiment of the invention is shown in FIG. 1. The system 100 can include a harvester 102 which can be mounted on the head of a rat 104. The harvester, which will be described in greater detail below, can be a thermoelectric energy harvester (TEH) which harvests energy by taking advantage of a temperature difference between two surfaces. In various embodiments, the harvester 102 can connect to a power management circuit 106. The power management circuit 106, which will be described in greater detail below, can control various functionalities of the harvester 102. In some embodiments, the power management circuit can store harvested energy. In many embodiments, a connector 108 can transfer the harvested energy from the subject to the power management circuit 106. Although more readily illustrated as a wired connector, the connection can be a wireless connection such as (but not limited to) an inductive connection. In various embodiments, the harvester 102 can be integrated directly into the power management circuit 106.

One of ordinarily skill in the art would appreciate that a TEH system is not specifically limited to integration with any particular subject or body part of the subject, but any living subject and/or body part can be utilized. Although specific power harvesting systems are discussed above with respect to FIG. 1, any of a variety of systems that harvest energy with TEHs as appropriate to the requirements of a specific application can be utilized in accordance with embodiments of the invention. Power management circuits for TEH systems in accordance with embodiments of the invention are discussed further below.

TEH Power Management Circuits

Figure 2:
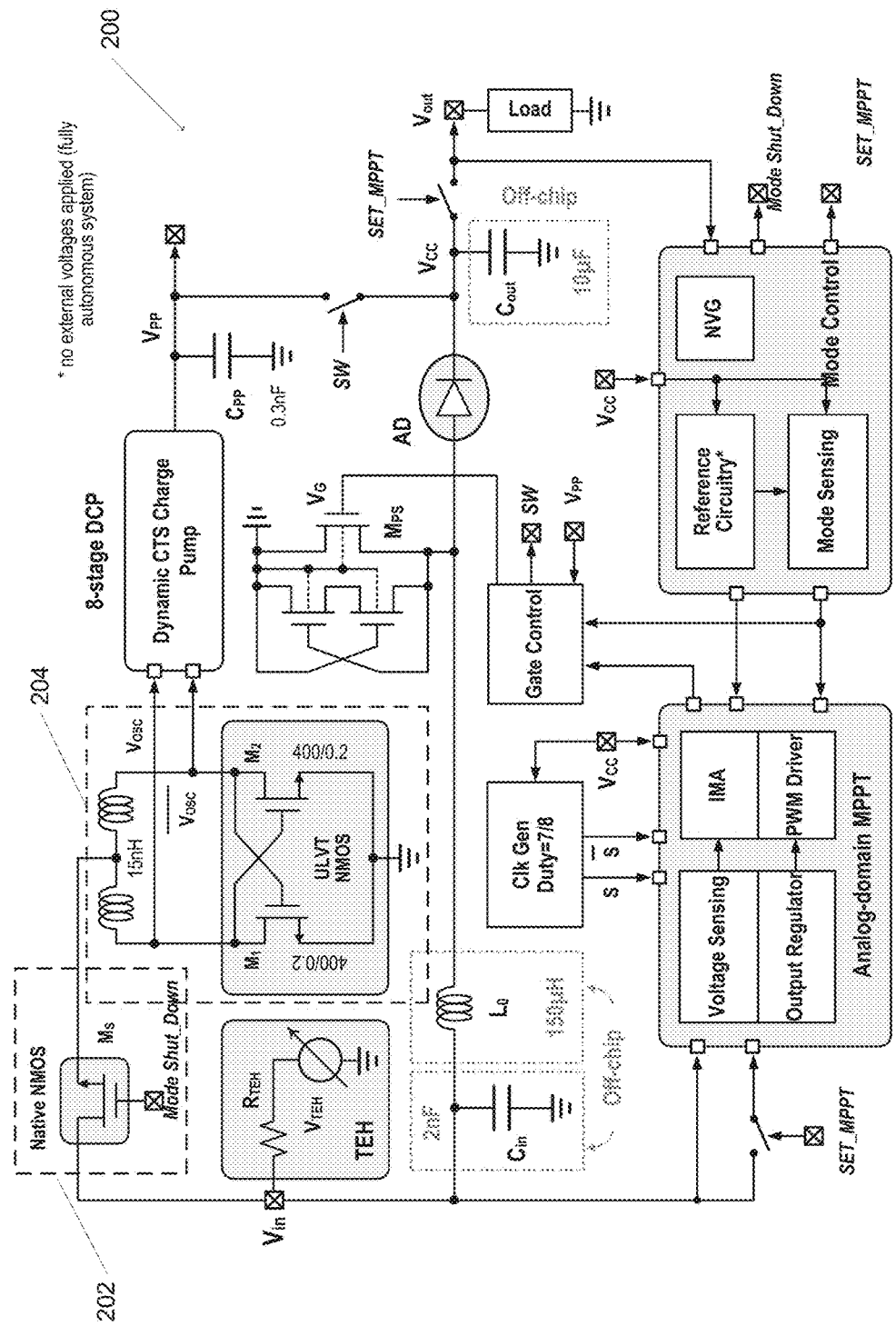
FIG. 2 is a schematic of a thermoelectric energy harvesting system in accordance with an embodiment of the invention.

A power management circuit can be integrated with a TEH for implementation in biomedical sensors. A block diagram of a power management circuit integrated with a compound TEH in accordance with an embodiment of the invention is shown in FIG. 2. In many embodiments, the power management circuit 200 utilizes a dual-mode boost converter to generate greater voltages using voltages generated based on the thermal gradient. In many embodiments, the power management circuit can operate in a start-up mode and a maximum-power-point-tracking (MPPT) mode. Typically, the start-up mode configures the power management circuit to harvest energy to initially charge the circuitry, and in various embodiments can do so by periodically alternating use of an upper and lower branch of the circuit as further discussed below. In various embodiments, the power management circuit can switch to a MPPT mode once a predetermined amount of energy has been harvested using the TEH, for example (but not limited to) when a certain voltage has been reached. In several embodiments, MPPT mode configures the power management circuit to maximize voltage generation in the TEH system as further discussed below.

In various embodiments, the dual-mode boost converter can utilize a shared single inductor to minimize area. Further, any intermediate boosting steps (as used in prior systems) can be eliminated by using power-efficient start-up modes as further described below.

In several embodiments, the circuit can include a start-up mode having a so-called "upper" and "lower" branch for improved efficiency. In many embodiments, the upper branch can be an on-chip circuitry, comprising a mode switch Ms 202 and inductive-load ring oscillator (ILRO) 204. In various embodiments, the ILRO 204 has low minimum operating voltage and low overall costs. Large-area off-chip inductors, that would additionally load the ILRO output and increase the start-up time and voltage, are generally avoided in many embodiments of the invention.

Typically, there is no initial energy in the circuit and the current generated from the TEH can flow through one of the start-up branches. Further, the mode switch 202 can be utilized to switch between the start-up mode and MPPT mode as further discussed below. In various embodiments, the mode switch can be realized as a native-NMOS (initially ON) that has a large negative $V_T$, while a cross-coupled pair $M_{1-2}$ can utilize high-performance ultralow-$V_T$ analog transistors. With a high current-drive of $M_{1-2}$ and sufficient voltage gain at very low supplies, the ILRO 204 can operate in weak inversion. Given GP, n, $g_{md}$ and $\varphi_t$ to model the inductor loss, the sub-threshold slope factor, $M_{1-2}$ transconductance and thermal voltage, respectively, the minimum $V_{start-up}$ to start-up the oscillator is $V_{start-up}(min) = \varphi_t \ln(1 + nG_P/g_{md})$.

In many embodiments, the TEH system can achieve $Q_{ILRO} = 10.5$ @ 300 MHz and a low $V_{start-up}$. The $V_{start-up}$ (min) model correlates well with simulated (60 mV) and measured (65 mV) data. Although specific power management circuits integrated with TEHs are discussed above with respect to FIG. 2, any of a variety of power management circuits for integration with TEHs as appropriate to the requirement of a specific application can be utilized in accordance with embodiments of the invention. Start-up modes for TEH systems in accordance with embodiments of the invention are discussed further below.

Start-Up Modes

Figure 3A:
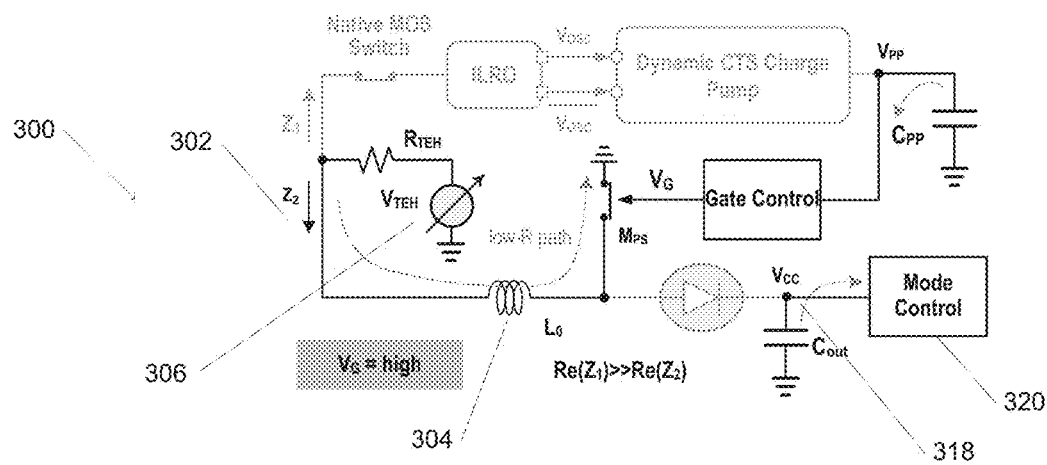
FIGS. 3A-3F are schematics and relevant time waveforms illustrating a start-up mode in accordance with an embodiment of the invention.

A TEH system can utilize various start-up modes for the charging phase of the system. A start-up mode with relevant time waveforms in accordance with an embodiment of the invention is illustrated in FIGS. 3A-3F. In many embodiments, during the charging phase the lower branch 300 is utilized as illustrated in FIG. 3A. When $V_G$=high, the current chooses the path of lower resistance 302 ($Z_2$), and the upper branch (comprising an ILRO and change pump illustrated in FIG. 3B) is not utilized. In many embodiments, this path of lower resistance, or the lower branch of the circuit, can include an inductor $L_0$ 304. The current from the TEH 306 flows into inductor $L_0$ 304 and is stored.

Figure 3B:
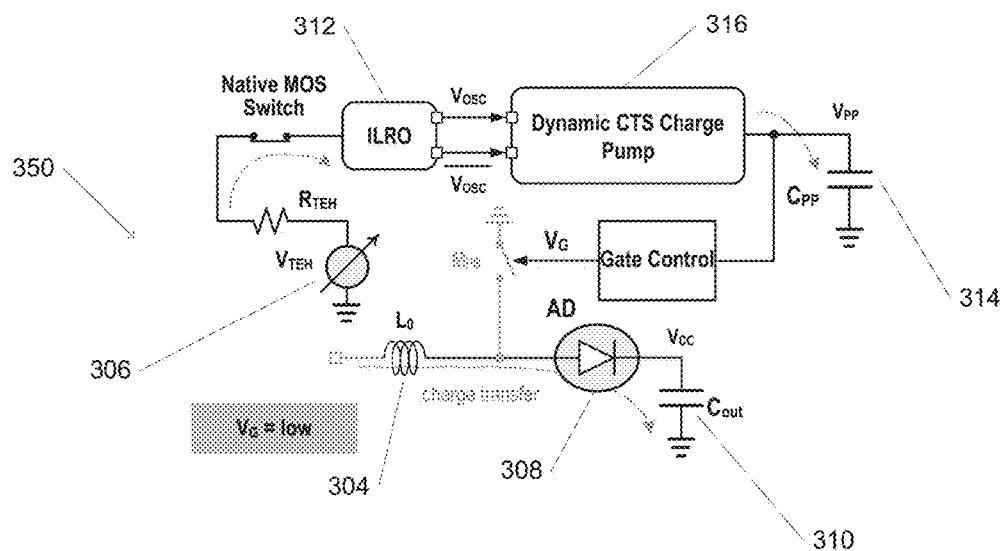

In several embodiments, when $V_G$=low the upper branch 350 is utilized as illustrated in FIG. 3B, and the lower branch comprising an inductor $L_0$ 304 and active diode 308 (AD) can be active. The energy stored in inductor $L_0$ 304 transfers through the AD 308 to an output capacitor $C_{out}$ 310. In several embodiments, the current from the TEH 306 flows into the ILRO 312 of the upper branch, which starts to oscillate and additionally refill a capacitor $C_{PP}$ 314 through the charge pump 316. In several embodiments, circuitry supplied from $C_{PP}$ 314 draws only 80 nA over one period.

Periodically, the upper branch turns ON and keeps boosting the output voltage $V_{CC}$ 318. In a variety of embodiments, when $V_{CC}$ 318 reaches 0.8V, the MPPT controller 320 can become active as further discussed below.

Figure 3C:
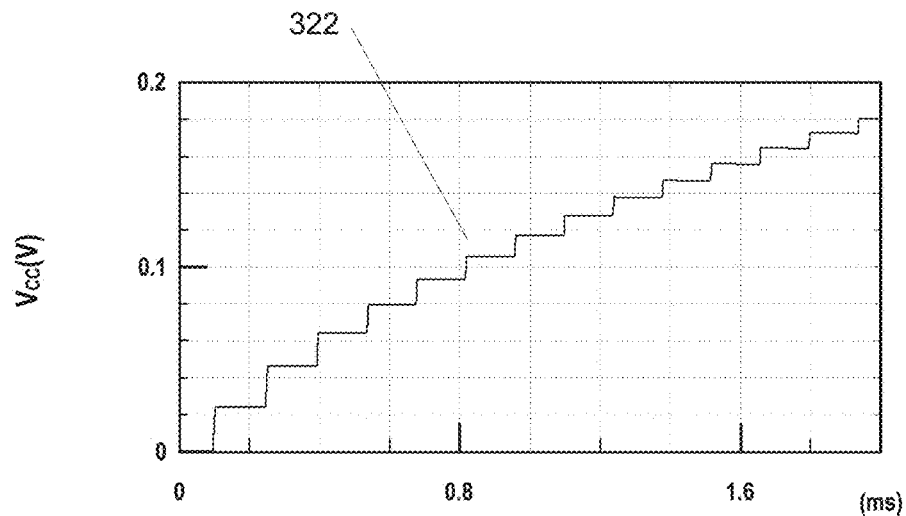
Figure 3D:
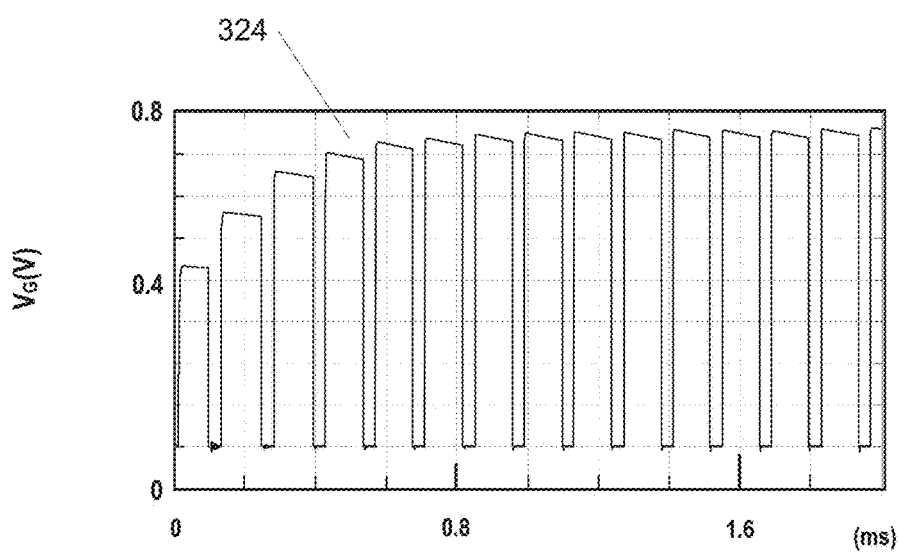
Figure 3E:
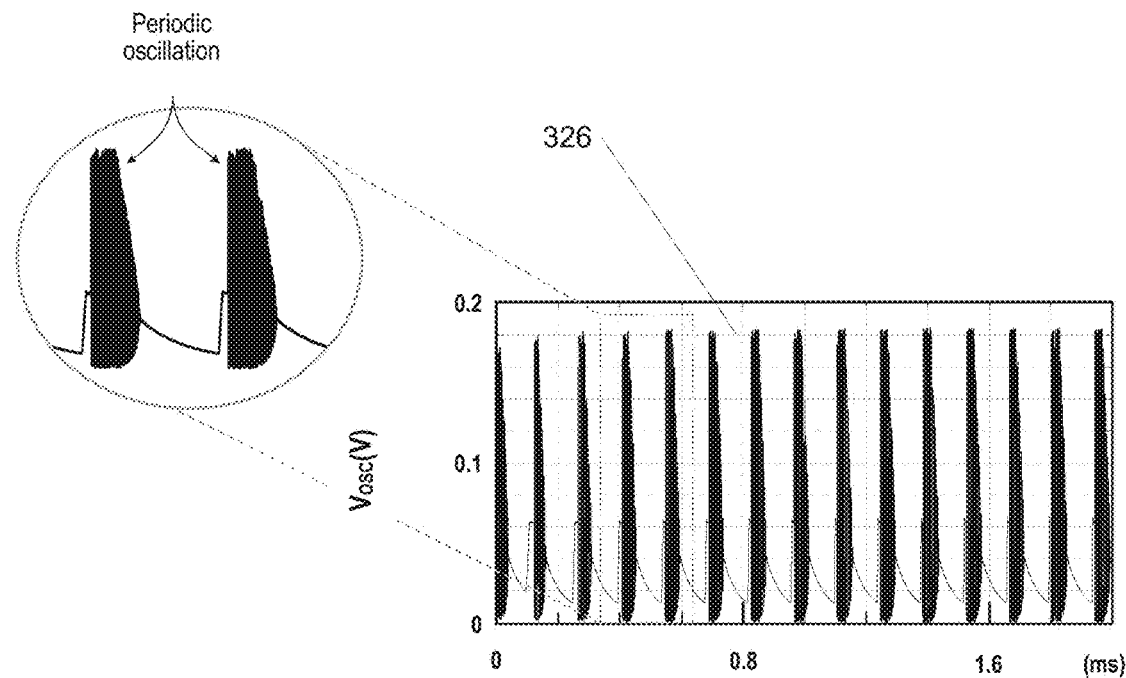
Figure 3F:
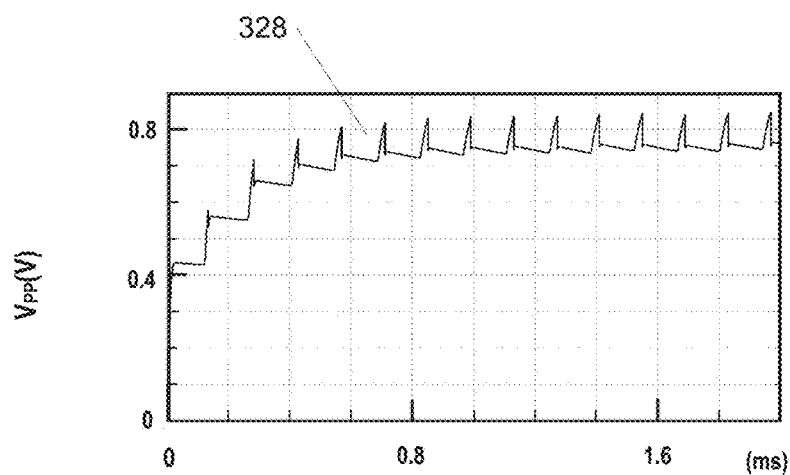

Waveforms corresponding to voltages throughout the system during start-up mode are illustrated in FIGS. 3C-3F. A voltage measure $V_{CC}$ 322 as a function of time is illustrated in FIG. 3C. A voltage measure $V_G$ 324 as a measure of time is further illustrated in FIG. 3D. FIG. 3E illustrates a voltage measure $V_{OSC}$ 326 as a function of time. Additionally, FIG. 3F illustrates a voltage measure $V_{PP}$ 328 as a function of time.

Although a specific start-up mode of TEH systems are discussed above with respect to FIGS. 3A-3F, any of a variety of start-up modes for use in TEH systems as appropriate to the requirements of a specific application can be utilized in accordance with embodiments of the invention. Maximum-power-point tracking (MPPT) modes for TEH systems in accordance with embodiments of the invention are discussed further below.

Maximum-Power-Point Tracking Modes

Figure 4A:
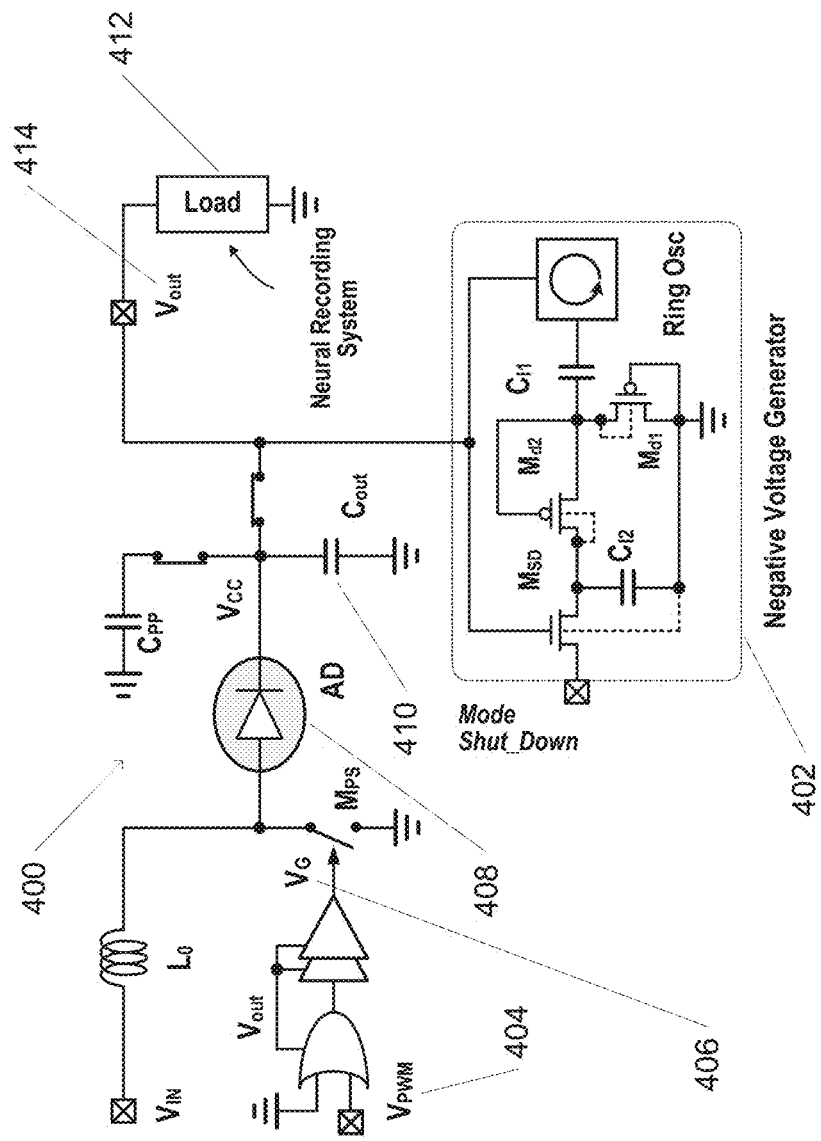
FIGS. 4A-4H are schematics and relevant time waveforms illustrating a maximum-power-point tracking (MPPT) mode in accordance with an embodiment of the invention.

A TEH system can utilize a so-called MPPT mode using an MPPT controller and MPPT loop. An MPPT loop architecture and relevant waveforms in accordance with an embodiment of the invention are shown in FIGS. 4A-4H. In many embodiments, after an MPPT controller 400 as illustrated in FIG. 4A becomes active (SET_MPPT=high), a negative voltage generator 402 can output −0.4V to shut down the mode switch and the start-up circuitry as described above. In various embodiments, a clock generator provides inputs S and $\bar{S}$ at a 600 μs period and 7/8 duty ratio.

In several embodiments, when the input S=low, the voltage sensor typically senses the open-circuit voltage $V_{TEH}$, while the pulse width modulator (PWM) and GC blocks hold $V_{PWM}$ 404 and $V_G$ 406 at zero, respectively. During this period, the AD 408 blocks the reverse current from $C_{out}$ 410.

In various embodiments, when the input S=high, a capacitive divider outputs $V_{TEH}/2$. In many embodiments, a comparator in the impedance-matching adapter $CMP_3$ 416 as illustrated in FIG. 4B dynamically matches $V_{in}$ 418 and $V_{TEH}/2$ 420, by adjusting the pulse width of $V_G$ through the PWM and GC blocks. In various embodiments, a fast voltage sensing ($C_{d1,2}$=50 pF) and $CMP_3$ 416 can enable the TEH system to find the maximum-point-point in a very short time (<20 ms for complete MPPT regulation). In many embodiments, a voltage ripple at $V_{in}$ due to the fast feedback-loop response can be mitigated with a small (2 nF) input capacitance $C_{in}$ which can typically be found off chip and a short settling time (3 μs) can be achieved. In several embodiments, a feedback loop can rapidly capture the fluctuations (up to 50 Hz) experienced at the harvester side. In various embodiments, the $V_{in}$ signal moves repeatedly between $V_{TEH}$ and $V_{TEH}/2$, verifying correct impedance matching and adaptive load-line tuning.

In many embodiments, the MPPT mode can be prolonged until $C_{out}$ is charged to a desired value including (but not limited to) 1.8V, which can be sufficient to power a load 412 such as a neural recording interface. In several embodiments, when the load 412 is attached, a comparator $CMP_2$ 422 can dynamically keep $V_{out}$ 414 at the desired level by alternating SET_OUT between the ON and OFF states. As an illustrative example a load can be a neural recording system, but any of a variety of loads powered by the TEH system can be utilized. In a variety of embodiments, the MPPT controller and all auxiliary circuitry consume 2.9 μA in active mode and 0.07 μA in idle mode, for improved efficiency.

Figure 4C:
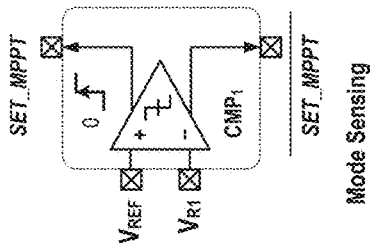
Figure 4B:
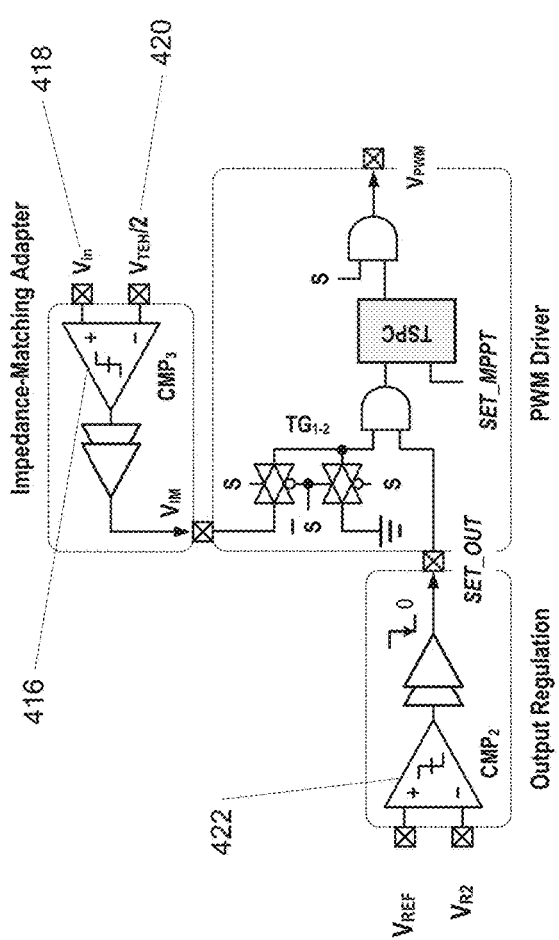
Figure 4D:
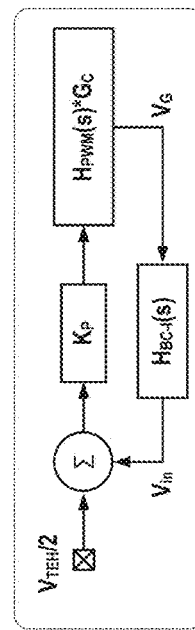
Figure 4E:
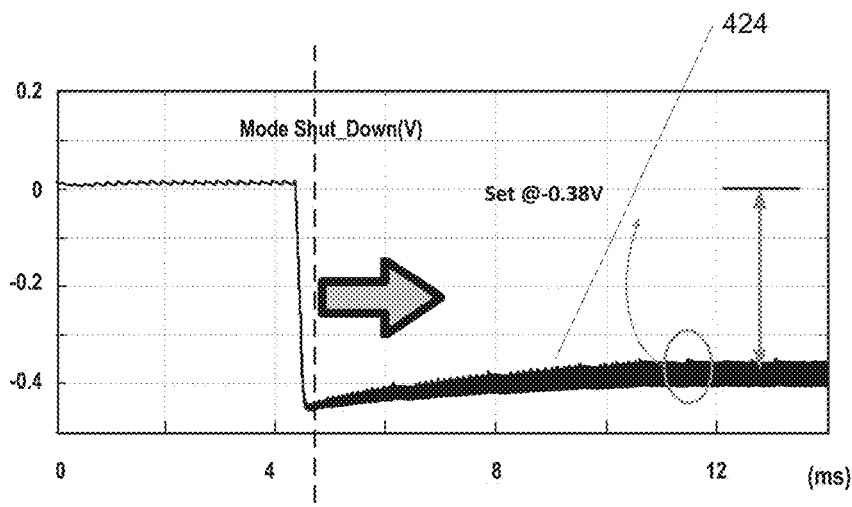
Figure 4F:
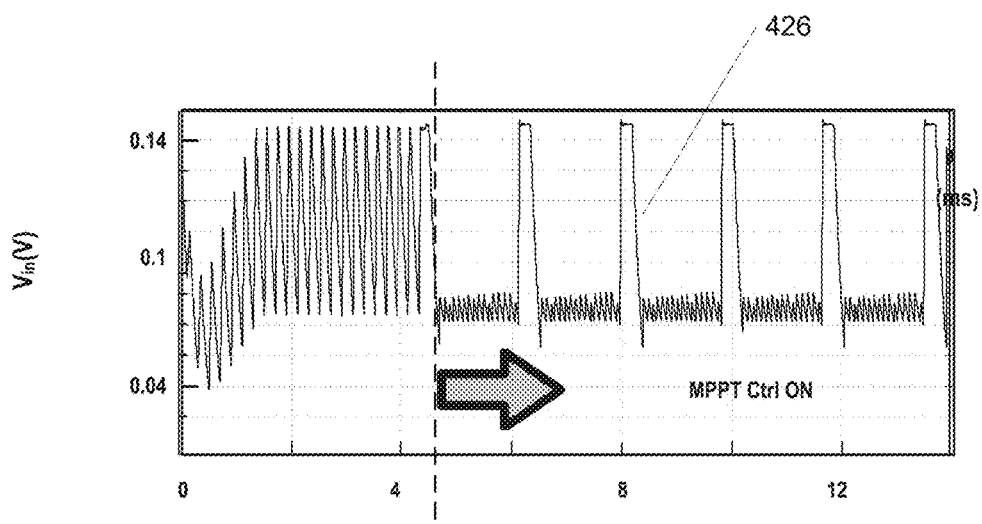
Figure 4G:
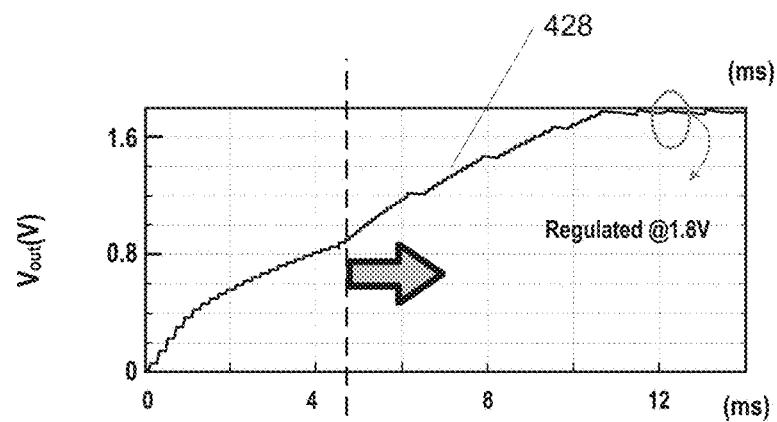
Figure 4H:
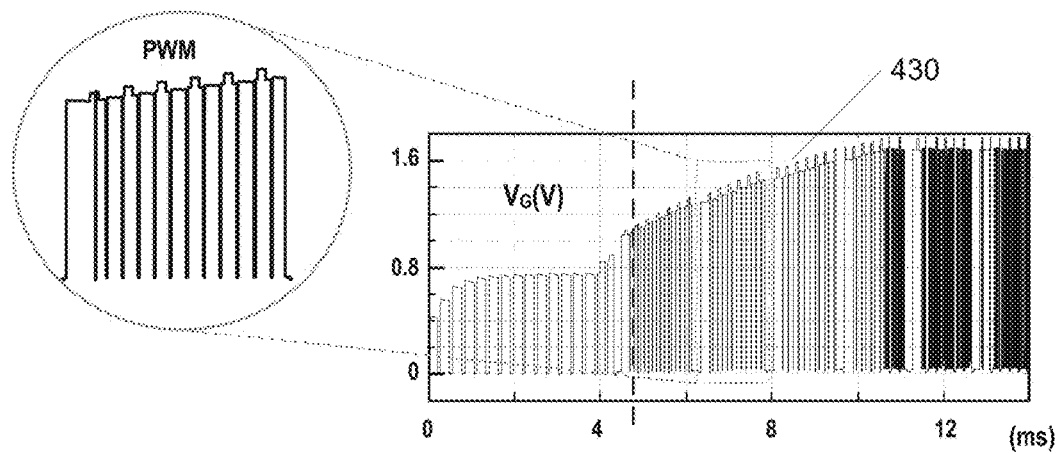

Mode sensing is illustrated in FIG. 4C. A linear model of MPPT mode is illustrated in FIG. 4D. Waveforms for various voltages throughout MPPT mode are further illustrated in FIGS. 4E-4H. A voltage measure Mode Shut_Down 424 as a measure of time is illustrated in FIG. 4E. A voltage measure $V_{IN}$ 426 as a measure of time is illustrated in FIG. 4F. FIG. 4G illustrates a voltage measure $V_{OUT}$ 428 as a measure of time. Additionally, FIG. 4H illustrates a voltage measure $V_G$ 430 as a measure of time.

Although a specific MPPT mode for use in TEH systems are discussed above with respect to FIGS. 4A-4H, any of a variety of MPPT modes for use in TEH systems as appropriate to the requirements of a specific application can be utilized in accordance with embodiments of the invention. Various TEH system components in accordance with embodiments of the invention are discussed further below.

Thermoelectric Energy Harvester System Components

Figure 5A:
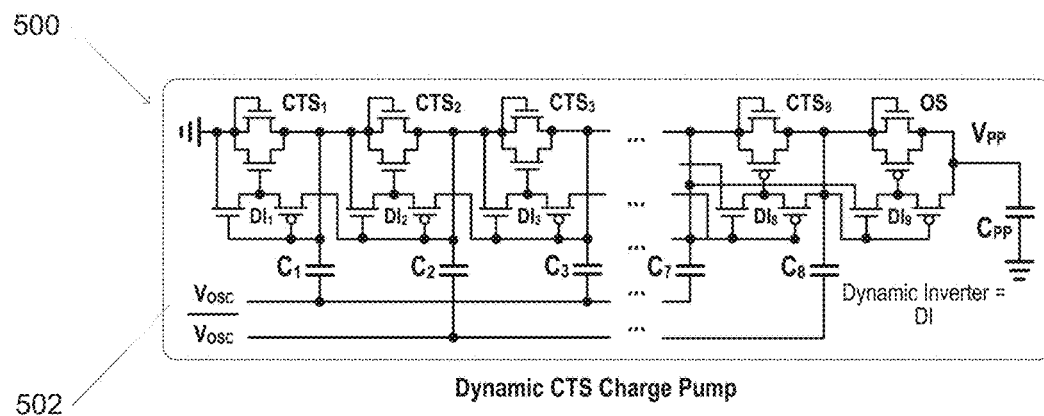
FIGS. 5A-5D are schematics of various components of a thermoelectric energy harvesting system in accordance with an embodiment of the invention.

A TEH system can utilize various components in realizing autonomous thermoelectric energy-harvesting systems for biomedical sensors. Circuit details of a charge pump are illustrated in FIG. 5A, gate control (GC) blocks are illustrated in FIG. 5B, and an AD are illustrated in FIG. 5C in accordance with an embodiment of the invention. In many embodiments, a dynamic charge-transfer-switch (CTS) charge pump 500 as illustrated in FIG. 5A can transfer charge from one stage to the next without incurring voltage drops. Typically, the pass transistors in the CTS stages can be turned OFF completely by a $V_{OSC}$ 502 and can also be turned ON effectively by the higher voltage generated in the next CTS stage. Thus, reverse charge flow can be avoided, leading to higher efficiency. The simulated power efficiency of an 8-stage charge pump in accordance with an embodiment of the invention can be from 41% ($V_{OSC}$=100 $mV_{pk-pk}$) to 71% ($V_{OSC}$=500 $mV_{pk-pk}$).

A GC block 520 is illustrated in FIG. 5B. When $V_{PP}$ 522 exceeds 0.3V, a thyristor-based oscillator (TRO) 524 can drive the buffer in the GC block to charge and discharge the power switch. A TRO 524 is typically used because it is robust to voltage variations and has low power consumption.

In several embodiments, the AD 540 as illustrated in FIG. 5C can turn ON with a near-zero voltage drop when $V_S$ 542>$V_O$ 544. Further, it can turn OFF immediately when $V_S$ 542<$V_O$ 544, preventing the reverse current leakage. In addition, the NMOS cross-coupled pair can form a positive feedback to create a bi-stable condition and provide tolerance for unwanted noise and input coupling ripples. In various embodiments, the transistors $M_{R1}$-$M_{R2}$ act as big resistors while $M_1$-$M_6$ control the gate voltage of $M_D$, effectively mimicking an ideal low-power Schottky diode. In a variety of embodiments, comparators can use folded-cascode self-biased OpAmps to optimize the power-gain tradeoff. In many embodiments, each comparator $CMP_1$-$CMP_3$ can consume <900 nA from a 1.8V supply, with ~60 dB gain.

Figure 5D:
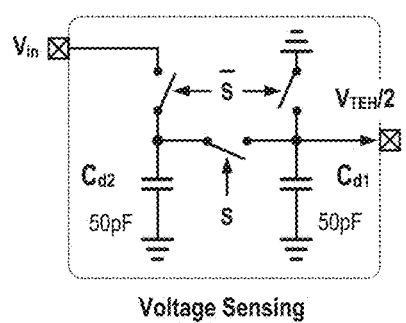
Figure 5C:
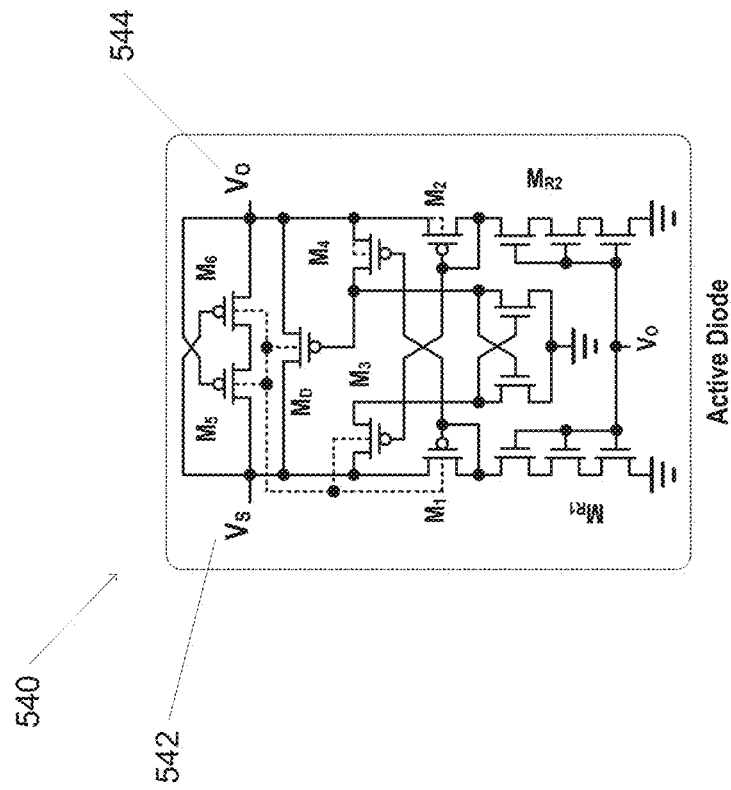
Figure 5B:
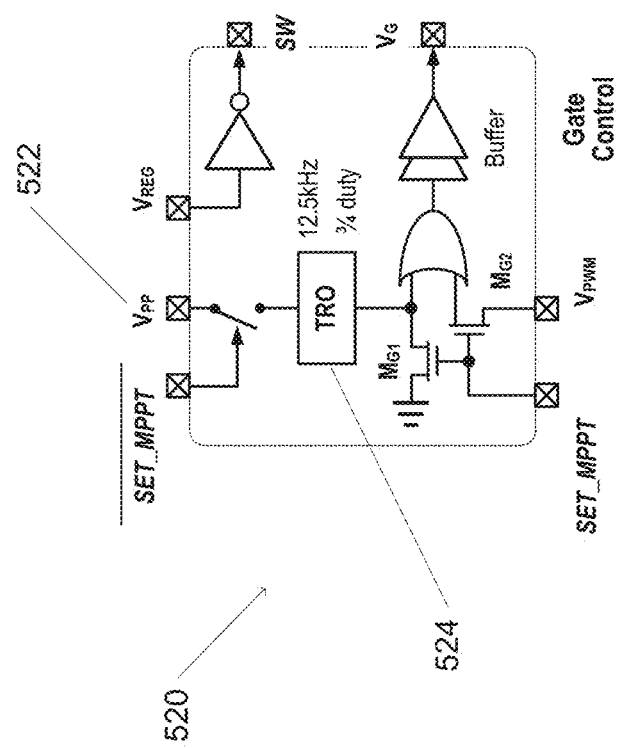

Voltage sensing is illustrated in FIG. 5D. Although specific components for use in autonomous thermoelectric energy-harvesting systems are discussed above with respect to FIG. 5A-5D, any of a variety of components for autonomous thermoelectric energy-harvesting systems as appropriate to the requirements of a specific application can be utilized in accordance with embodiments of the invention. Thermoelectric energy harvesters in accordance with many embodiments of the invention are described further below.

Figure 6:
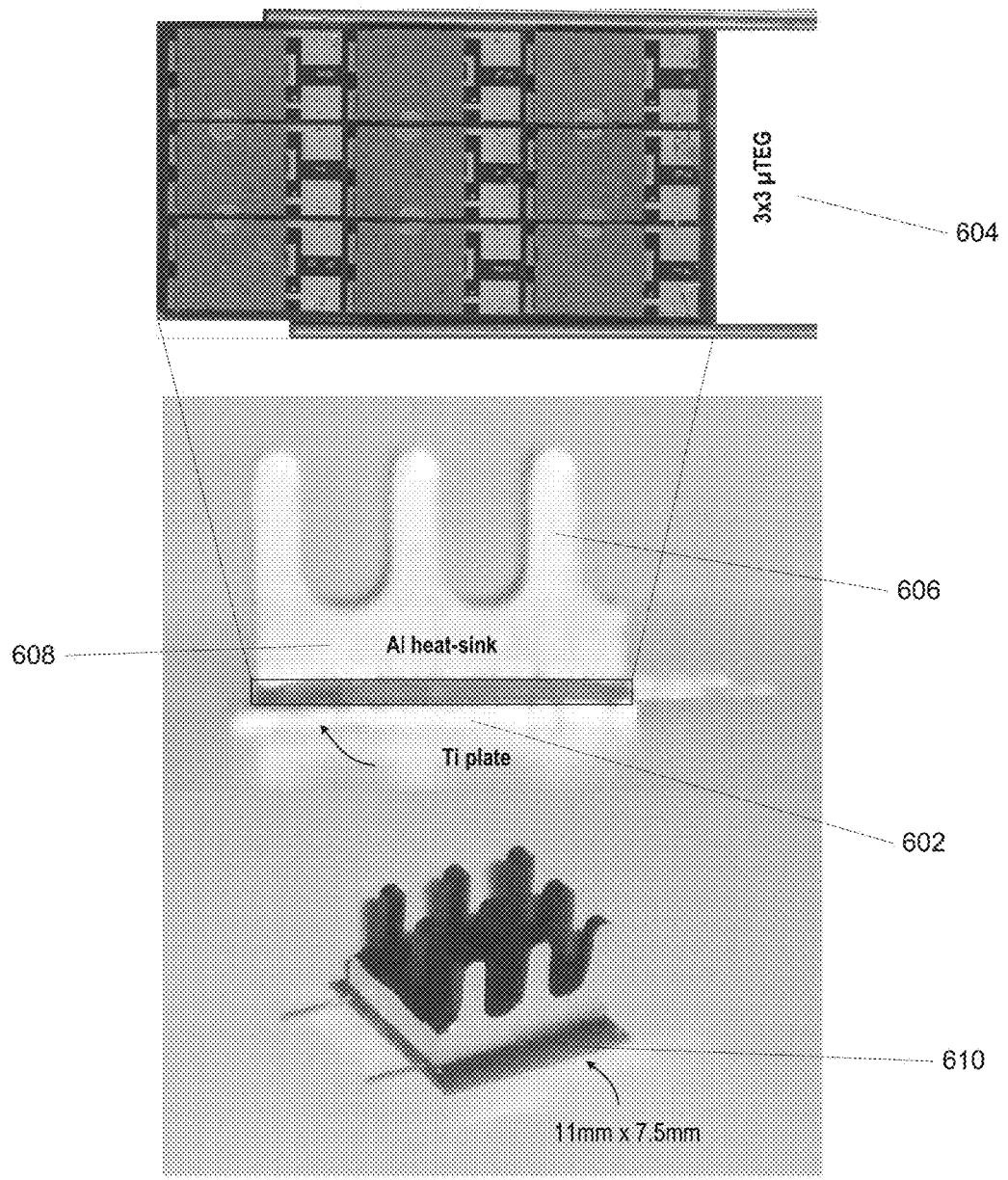
FIG. 6 illustrates a fabricated compound thermoelectric energy harvester (TEH) in accordance with an embodiment of the invention.
Figure 7:
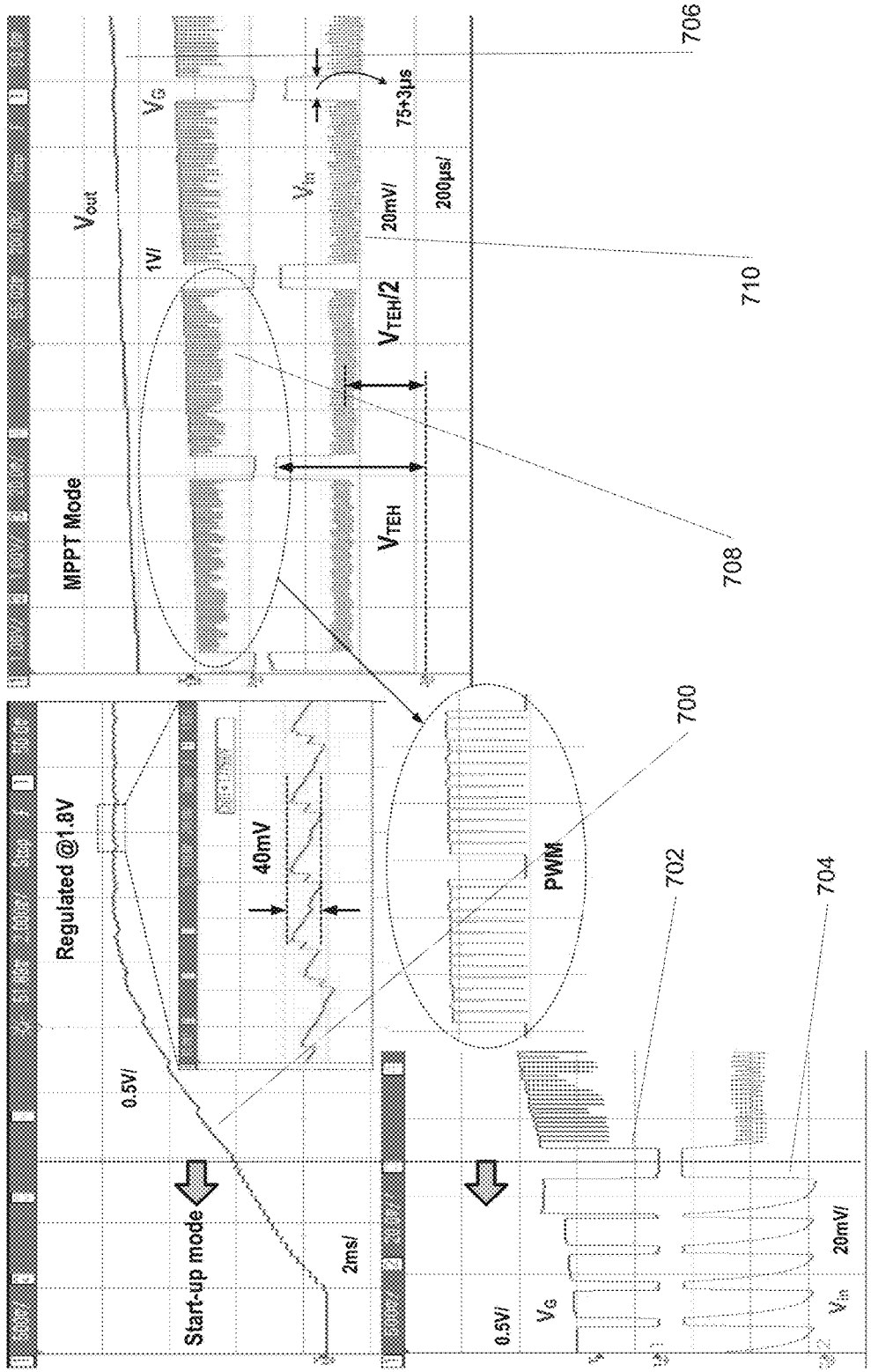
FIG. 7 is a graph illustrating results obtained in accordance with an embodiment of the invention.

A TEH system can be designed and fabricated to meet the biophysical and anatomical constraints of various living subjects including (but not limited) to a rat. A thermoelectric energy harvester and associated waveforms in accordance with an embodiment of the invention is illustrated in FIG. 6 and FIG. 7. A harvester is illustrated in FIG. 6. In many embodiments, a bottom titanium plate 602 can be configured to directly contact an animal's cerebrovascular system using a 3×3 electrical μTEGs arrangement 604. Each μTEG 606 serves as an independent voltage source. By stacking three μTEGs and connecting the stacks in parallel the output power can be increased while the equivalent source impedance decreases. In various embodiments, measurements show that the TEH structure has an internal impedance of 6.3Ω. In several embodiments, a 11 mm×7.5 mm heat sink 608 can be utilized which is large enough to cover all three TEGs, while the bottom plate extends 1 mm on two sides 610 to accommodate skull-fixing screws. Further, a biocompatible insulator can be applied to the exposed space between the plate and the heat sink to prevent heat leakage.

As illustrated, the harvesting platform can be mounted on the head of a rat. In many embodiments, a temperature gradient of 3.5K is observed and the system was able to harvest 645 μW regulated output power, with 60% end-to-end (92% converter) efficiency, at VTEH=170 mV. In various embodiments, a temperature gradient of 3.5K is observed and the system was able to harvest 645 μW regulated output power, with 60% end-to-end (92% converter) efficiency, at VTEH=170 mV. FIG. 7 illustrates measured lab waveforms for a harvesting platform for voltage measures $V_{out}$ 700, $V_G$ 702, and $V_{in}$ 704 during start-up mode and $V_{out}$ 706, $V_G$ 708, and $V_{in}$ 710 during MPPT mode as a function of time in accordance with an embodiment of the invention.

Although specific TEH harvesters are discussed above with respect to FIG. 6 and FIG. 7, any of a variety of energy harvesters for biomedical and/or other applications can be utilized as appropriate to the requirements of specific applications in accordance with embodiments of the invention. Design considerations and results for TEH systems in accordance with many embodiments of the invention are discussed further below.

Design Considerations and Results

A comparison with previous designs in accordance with an embodiment of the invention is shown in FIG. 8. In several embodiments, a peak end-to-end efficiency was measured at 68% at $V_{TEH}$=220 mV, outperforming previous designs. In various embodiments, the miniaturized harvesting platform in accordance with embodiments of the invention showed a 7.9× improvement in regulated power density relative to previous designs. In many embodiments, improved efficiency can be attributed to the integrated power-efficient start-up module, the fast fully-analog MPPT controller, and the compact TEH source. Measured signals during the MPPT control indicate fully-autonomous operation down to $V_{TEH}$=65 mV. As illustrated, the comparisons are made using [1] E. J. Carlson, et. al., "20 mV Input Boost Converter With Efficient Digital Control for Thermoelectric Energy Harvesting," *IEEE JSSC, vol.* 45, no. 4, pp. 741-750, April 2010, [2] Y. K. Ramadass and A. P. Chandrakasan, "A Batteryless Thermoelectric Energy-Harvesting Interface Circuit with 35 mV Startup Voltage," *ISSCC* 2010, pp. 486-487, [3] J.-P. Im, et. al., "A 40 mV Transformer-Reuse Self-Startup Boost Converter with MPPT Control for Thermoelectric Energy Harvesting," *ISSCC* 2012, pp. 104-106, and [4] H.-Y. Tang, et. al., "A Fully Electrical Startup Batteryless Boost Converter with 50 mV Input Voltage for Thermoelectric Energy Harvesting," *VLSI* 2012, pp. 196-197.

Figure 9:
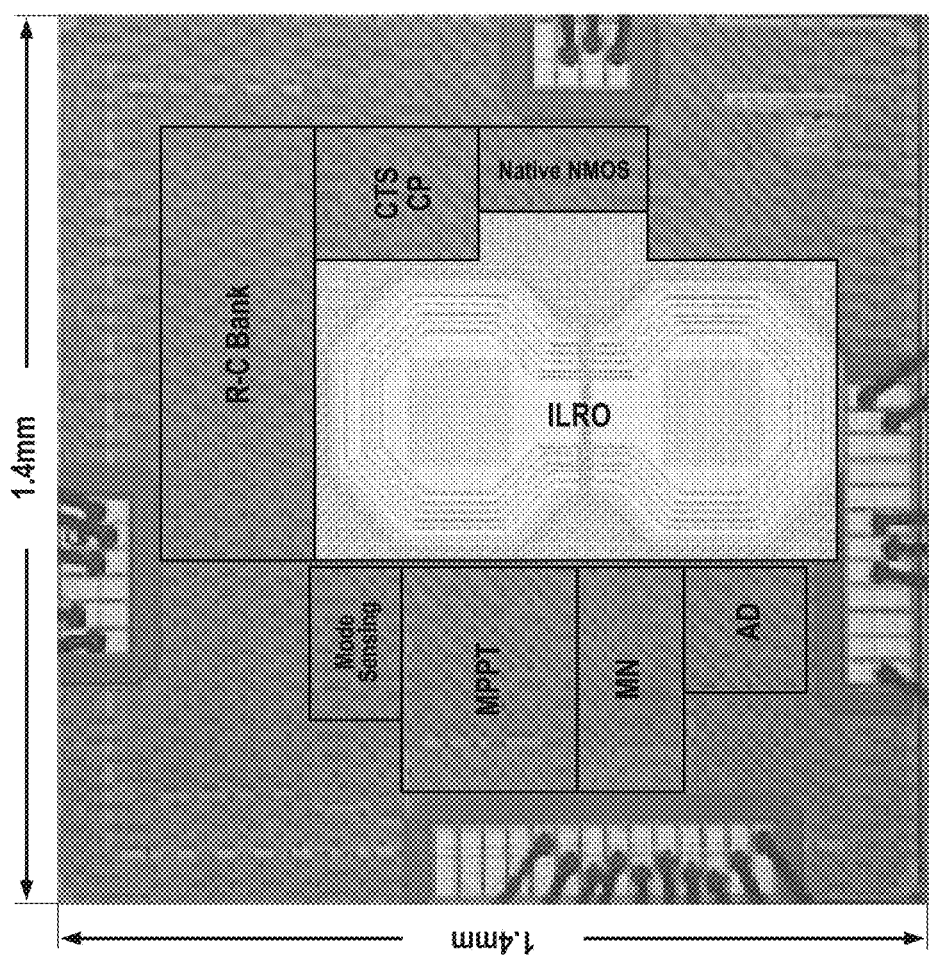
FIG. 9 illustrates a chip micrograph in accordance with an embodiment of the invention.

An illustrative micrograph of a chip fabricated in a 65 nm CMOS process with MPPT controller occupying 0.06 mm² and startup circuitry occupying 0.65 mm² is shown in FIG. 9. In many embodiments, the printed circuit board (PCB) utilizes only one off-chip inductor and one storage capacitor, which allows miniaturization. In several embodiments, a small PCB together with the compound TEH occupy <1 cm³ and weigh <3 g. In various embodiments, TEH platforms in accordance with embodiments of the invention offer superior power density levels and form factor that can eliminate conventional batteries in size-constrained neural recording applications.

Figure 10:
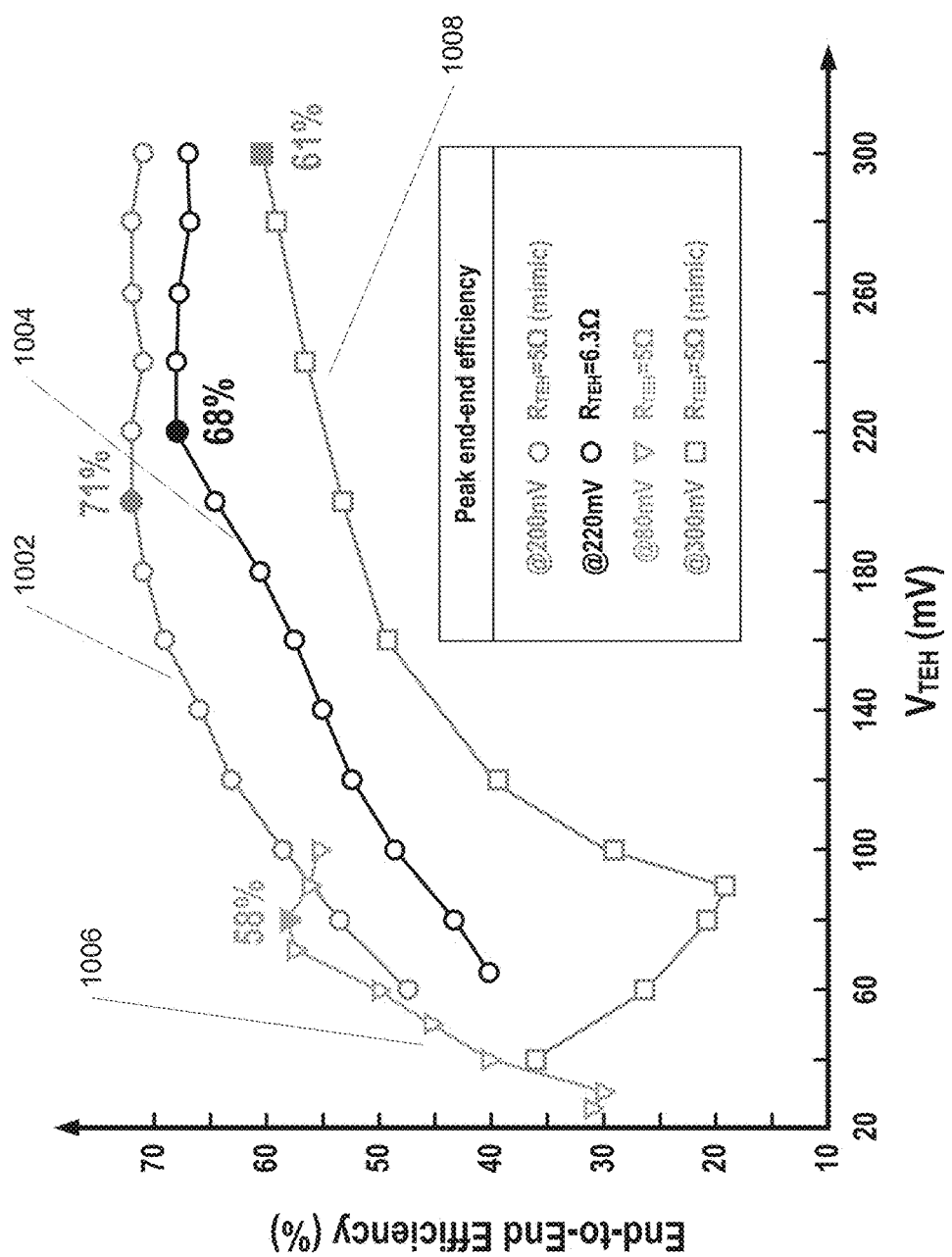
FIG. 10 is a graph illustrating measured end-to-end efficiency in comparison to previous works in accordance with an embodiment of the invention.

A graph illustrating measured end-to-end efficiency in comparison to previous designs in accordance with an embodiment of the invention is illustrated in FIG. 10. Systems in accordance with embodiments of the invention are illustrated in 1002, 1004. As illustrated, the comparisons are made in reference to 1006 (Y. K. Ramadass and A. P. Chandrakasan, "A Batteryless Thermoelectric Energy-Harvesting Interface Circuit with 35 mV Startup Voltage," *ISSCC* 2010, pp. 486-487,) and 1008 (J.-P. Im, et. al., "A 40 mV Transformer-Reuse Self-Startup Boost Converter with MPPT Control for Thermoelectric Energy Harvesting," *ISSCC* 2012, pp. 104-106).

Figure 11:
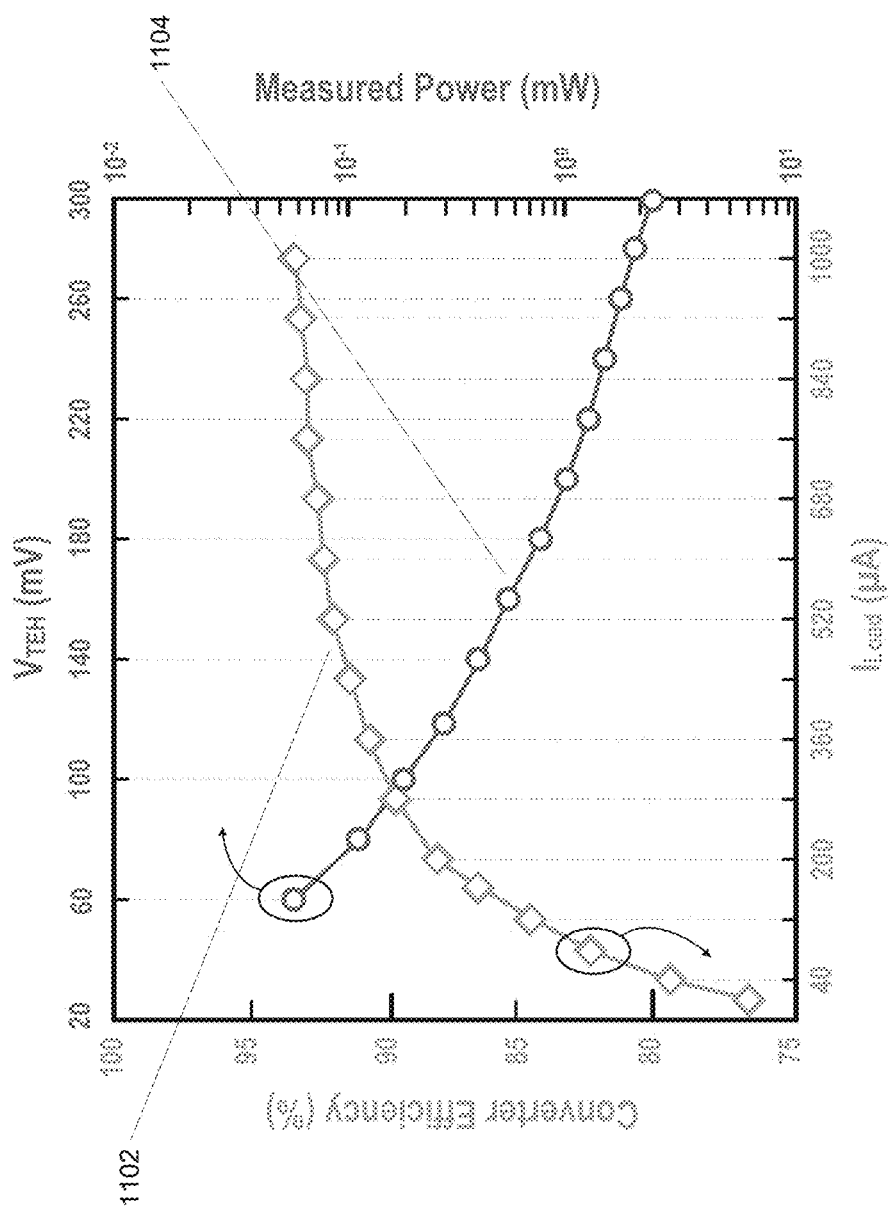
FIG. 11 is a graph illustrating measured converter efficiency as a function of an output load current, and measured output power as a function of a source voltage in accordance with an embodiment of the invention.

A graph illustrating measured converter efficiency 1102 as a function of an output load current $I_{Load}$, and measured output power 1104 as a function of a source voltage $V_{TEH}$ in accordance with an embodiment of the invention is illustrated in FIG. 11.

A chart illustrating some drawbacks of previous TEH designs in accordance with an embodiment of the invention is illustrated in FIG. 12. As illustrated in FIG. 12, the comparisons are made relative to [1] E. J. Carlson, et. al., "20 mV Input Boost Converter With Efficient Digital Control for Thermoelectric Energy Harvesting," *IEEE JSSC*, vol. 45, no. 4, pp. 741-750, April 2010, [2] Y. K. Ramadass and A. P. Chandrakasan, "A Batteryless Thermoelectric Energy-Harvesting Interface Circuit with 35 mV Startup Voltage," *ISSCC* 2010, pp. 486-487, [3] J.-P. Im, et. al., "A 40 mV Transformer-Reuse Self-Startup Boost Converter with MPPT Control for Thermoelectric Energy Harvesting," *ISSCC* 2012, pp. 104-106, [4] H.-Y. Tang, et. al., "A Fully Electrical Startup Batteryless Boost Converter with 50 mV Input Voltage for Thermoelectric Energy Harvesting," *VLSI* 2012, pp. 196-197, and [*] P.-H Chen, et. al., "A 95 mV-startup Step-up Converter with $V_{TH}$-tuned Oscillator by Fixed-charge Programming and Capacitor Pass-on Scheme," *ISSCC* 2011, pp. 216-217.

Although specific design considerations for TEH systems and measured results are discussed above with respect to FIGS. 8-12, any of a variety of design considerations and implementations as appropriate to the requirements of a specific application can be utilized in accordance with embodiments of the invention. While the above description contains many specific embodiments of the invention, these should not be construed as limitations on the scope of the invention, but rather as an example of one embodiment thereof. It is therefore to be understood that the present invention may be practiced otherwise than specifically described, without departing from the scope and spirit of the present invention. Thus, embodiments of the present invention should be considered in all respects as illustrative and not restrictive.

What is claimed is:

1. A thermoelectric energy harvesting system comprising:
    a thermoelectric energy harvester (TEH) comprising a thin-film array-based TEH source and a heat sink;
    start-up mode circuitry connected to the TEH comprising:
        an upper branch comprising:
            a mode switch configured to allow selection of the upper branch;
            an inductive-load ring oscillator (ILRO) comprising a cross-coupled pair, where the ILRO is configured to operate in weak inversion conditions;
            a charge pump configured to receive an input from the ILRO and output a current, where the output current is utilized to charge an upper branch capacitor;
        a lower branch comprising:
            an inductor;
            an active diode configured to transfer energy stored in the inductor to an output capacitor;
    maximum-power-point tracking (MPPT) mode circuitry comprising an MPPT controller configured to activate an MPPT loop, where the MPPT loop comprises:
        a mode control unit;
        a gate controller;
        a clock generator configured to generate at least one control signal;
        an analog-domain MPPT unit configured to receive the at least one generated control signal.

2. The thermoelectric energy harvesting system of claim 1, wherein the mode switch includes a native-NMOS that is initially set as ON.

3. The thermoelectric energy harvesting system of claim 1, wherein the cross-coupled pair utilizes analog transistors.

4. The thermoelectric energy harvesting system of claim 1, wherein the charge pump is an eight stage dynamic change-transfer-switch charge pump.

5. The thermoelectric energy harvesting system of claim 1, wherein the mode control unit comprises a negative voltage generator, mode sensing circuitry, and reference circuitry.

6. The thermoelectric energy harvesting system of claim 1, wherein the negative voltage generator is configured to shut down the mode switch and the start-up circuitry.

7. The thermoelectric energy harvesting system of claim 1, wherein the analog-domain MPPT unit comprises a voltage sensor, output regulator, a pulse width modulation driver, and an inversion matrix unit.

8. The thermoelectric energy harvesting system of claim 1, wherein the inductor is off-chip.

9. The thermoelectric energy harvesting system of claim 1, wherein the output capacitor is off-chip.

10. The thermoelectric energy harvesting system of claim 1, wherein a start-up mode stays active until the output capacitor has a value of 0.8V.

11. The thermoelectric energy harvesting system of claim 1, further comprising a load powered by the output capacitor.

12. The thermoelectric energy harvesting system of claim 11, wherein the load is a neural recording system.

13. The thermoelectric energy harvesting system of claim 1, wherein the upper branch periodically turns ON to boost the energy stored in the output capacitor.

14. The thermoelectric energy harvesting system of claim 1, wherein a MPPT mode stays active until the output capacitor is charged to a predetermined value based upon the at least one generated control signal.

* * * * *